(12) United States Patent
Switzer et al.

(10) Patent No.: US 6,800,475 B1
(45) Date of Patent: Oct. 5, 2004

(54) ISOLATION OF A HUMAN RETROVIRUS

(75) Inventors: William M. Switzer, Stone Mountain, GA (US); Walid Heneine, Atlanta, GA (US); Paul A. Sandstrom, Decatur, GA (US); Thomas M. Folks, Lithonia, GA (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 11 days.

(21) Appl. No.: 10/018,627

(22) PCT Filed: Jun. 14, 2000

(86) PCT No.: PCT/US00/16433
§ 371 (c)(1),
(2), (4) Date: Dec. 14, 2001

(87) PCT Pub. No.: WO00/77177
PCT Pub. Date: Dec. 21, 2000

Related U.S. Application Data
(60) Provisional application No. 60/139,219, filed on Jun. 14, 1999.

(51) Int. Cl.$^7$ ................................................ C12N 7/00
(52) U.S. Cl. ................ 435/235.1; 435/69.1; 435/320.1; 536/23.1; 536/23.72
(58) Field of Search ............................ 435/69.1, 235.1, 435/320.1; 536/23.1, 23.72

(56) References Cited

U.S. PATENT DOCUMENTS

| | | |
|---|---|---|
| 5,108,920 A | 4/1992 | Ng et al. |
| 5,459,056 A | 10/1995 | Powell et al. |
| 5,597,896 A | 1/1997 | Montagnier et al. |
| 5,646,032 A | 7/1997 | ter Meulen et al. |
| 5,882,912 A | 3/1999 | Sandstrom et al. |

FOREIGN PATENT DOCUMENTS

| | | |
|---|---|---|
| DE | 43 18387 | 12/1994 |
| WO | WO 98/35024 | 8/1998 |
| WO | WO 00/77177 | 12/2000 |

OTHER PUBLICATIONS

Shenk J General Virology 1999 vol. 80, pp. 1591–1598.*
Ali et al. No evidence of antibody to human foamy virus in widespread human populations. *AIDS Res. & Human Retrov.* 12(15):1473–1483 (1996).
Anonymous Survey for Simian Immunodeficiency Virus (SIV) Seropositivity in SIV—Laboratory Researchers—U. S., 1992. *MMWR Morb. Mort. Wkly Rep.* 41(43):814–815 (1988).
Callahan et al. Persistent Zoonotic Infection of a Human with Simian Foamy Virus in the Absence of an Intact orf–2 Accessory Gene. *J. of Virol.* 73(11):9619–9624 (Nov. 1999).
Chapman et al. Xenotransplantation and xenogeneic infections. *N. Engl. J. Med.* 333:1498–1501 (Nov.30, 1995).
Cordonnier et al. Isolation of Novel Human Endogenous Retrovirus–Like Elements with Foamy Virus–Related pol Sequence. *J. of Virol.* 69(9):5890–5897 (Sep. 1995).
DHHS. Docket No. 96M–0311. Draft Public Health Service (PHS) Guideline on Infectious Disease Issues in Xenotransplantation. *Federal Register*61(185) (Sep. 23, 1996).
EMBL Database; EMVRL:AF049085; Accession No. AF049085 (Aug. 4, 1998).
EMBL Database; EMVRL; AF049084; Accession No. AF049084 (Aug. 4, 1998).
Giron et al. Human Foamy Virus Polypeptides: Identification of *env*and *bel*Gene Products. *J. of Virol.* 67(6):3596–3600 (Jun. 1993).
Hahn et al. Reactivity of primate sera to foamy virus Gag and Bet proteins. *J. of Gen. Virology* 75:2635–2644 (1994).
Heneine et al. Absence of evidence for human spumaretrovirus sequences in patients with Graves' disease [letter]. *J. Acq. Immune Defic. Synd. & Human Retrov* 9:99–101 (1995).
Heneine et al. Identification of a human population Infected with simian foamy viruses. *Nat. Med.* 4(4):403–407 (Apr. 1998).
Heneine et al. Detection of reverse transcriptase by a highly sensitive assay in sera from persons infected with Human Immunodeficiency Virus Type–1. *J. Infect. Dis.* 171:1210–1216 (May 1995).
Heneine et al. Lack of evidence for infection with known human and animal retroviruses in patients with chronic fatigue syndrome. *Clin. Infec. Dis.* 18(Suppl. 1):S121–125 (1994).
Herchenroder et al. Isolation, Cloning and Sequencing of Simian Foamy Viruses from Chimpanzees (SFVcpz): High Homology Human Foamy Virus (HFV). *Virology.* 201:187–199 (1994).
Hirata et al. Transduction of Hematopoietic Cells by Foamy Virus Vectors. *Blood.* 88(9):3654–3661 (Nov. 1, 1996).

(List continued on next page.)

*Primary Examiner*—James Housel
*Assistant Examiner*—Myron G. Hill
(74) *Attorney, Agent, or Firm*—Needle & Rosenberg, P.C.

(57) ABSTRACT

The present invention comprises compositions and methods comprising a spumavirus isolated from a human. More specifically, the spumavirus of the present invention was isolated from a human who had exposure to nonhuman primates. Importantly, the methods and compositions of the present invention comprising the spumavirus and including antibodies to the spumavirus, can be used to detect the presence of spumavirus or antibodies in body fluids, for pathogenicity studies of related viruses, and as a vector for gene therapies. The present invention can also be used for treatment of conditions in humans due to the presence of rapidly dividing cells and for recombinant live virus vaccination.

8 Claims, 4 Drawing Sheets

OTHER PUBLICATIONS

Hooks et al. The Foamy Viruses. *Bacteriological Reviews.* 39(3):169–185 (Sep. 1975).

Khabbaz et al. Simian immunodeficiency virus needlestick accident in a laboratory worker. *Lancet* 340:271–273 (Aug. 1, 1992).

Khabbaz et al. Brief report: Infection of a laboratory worker with simian immunodeficiency virus. *N. Eng. J. Med.* 330:172–177 (Jan. 20, 1994).

Loh. Spumaviruses. *The Retroviridae.* 2:361–397 (1993).

Mahnke et al. Specific enzyme–linked immunosorbent assay for the detection of antibodies to the human spumavirus. *J. of Virological Methods.* 29:13–22 (1990).

McClure et al. Isolation of a New Foamy Retrovirus from Orangutans. *J. of Virol.* 68(11):7124–7130 (Nov. 1994).

Mergia et al. Cell tropism of the simian foamy virus type 1 (SFV–1). *J. Med. Primatology.* 25:2–7 (Jul. 21, 1995).

Neumann–Haefelin et al. Nonhuman Primate Spumavirus Infections Among Persons with Occupational Exposure. *MMWR Morb. Mort. Wkly Rep.* 46(6):129–131.

Neumann–Haefelin et al. Foamy viruses. *Intervirology* 35:196–207 (1993).

Latimore et al. Perspectives in Disease Prevention and Health Promotion Guidelines to Prevent Simian Immunodeficiency Virus Infection in Laboratory Workers and Animal Handlers. *MMWR Morb. Mort. Wkly Rep.* 37(45):693–694, 699–704 (Nov. 18, 1988).

Renne et al. Genomic Organization and Expression of Simian Foamy Virus Type 3 (SFV–3). *Virology* 186:597–608 (1992).

Russell et al. Foamy Virus Vectors. *J. of Virology* 70(1):217–222 (Jan. 1996).

Schweizer et al. Phylogenetic Analysis of Primate Foamy Viruses by Comparison of pol Sequences. *Virology* 207:577–582 (1995).

Schweizer et al. Markers of foamy virus infections in monkeys, apes, and accidentally infected humans: Appropriate testing fails to confirm suspected foamy virus prevalence in humans. *AIDS Res. & Human Retrov.* 11(1):161–170 (1995).

Schweizer et al. Simian foamy virus isolated from an accidentally infected human individual. *J. Virol.* 71(6):4821–4824 (Jun. 1997).

Schweizer et al. Absence of foamy virus DNA in Graves' disease. *AIDS Res. & Human Retrov.* 10(5):601–605 (1994).

Simonsen et al. Absence of evidence for infection with the human spumaretrovirus in an outbreak of Meniere–like vertiginous illness in Wyoming, USA [letter]. *ACTA Oto–Laryngologica* 114:223–224 (1994).

Weissenberge et al. Identification and Characterization of the Bel 3 Protein of Human Foamy Virus. *AIDS Res. And Human Retrov.* 10(5):595–600 (1994).

* cited by examiner

Case 6/Chimp Sequence Analysis (% identity)

integrase (425 bp)

|        | B1    | A055 | A101 | A136 | A182 |
|--------|-------|------|------|------|------|
| Case 6 | 100.0 | 92.7 | 93.6 | 92.5 | 93.4 |
| B1     | -     | 92.7 | 93.6 | 92.5 | 93.4 |
| A055   | -     | -    | 98.1 | 97.9 | 98.4 |
| A101   | -     | -    | -    | 97.9 | 98.4 |
| A136   | -     | -    | -    | -    | 98.4 |
| A182   | -     | -    | -    | -    | -    | gag (610 bp)

|        | B1    | A055 | A101 | A136 | A182 |
|--------|-------|------|------|------|------|
| Case 6 | 100.0 | 84.7 | 84.7 | 84.4 | 84.7 |
| B1     | -     | 84.7 | 84.7 | 84.4 | 84.7 |
| A055   | -     | -    | 98.1 | 96.7 | 97.5 |
| A101   | -     | -    | -    | 96.7 | 96.9 |
| A136   | -     | -    | -    | -    | 98.9 |
| A182   | -     | -    | -    | -    | -    |

ORF-2 (240 bp)

|        | B1   | A055 | A101 | A136 | A182 |
|--------|------|------|------|------|------|
| Case 6 | 94.1 | 82.4 | 82.0 | 82.0 | 82.9 |
| B1     | -    | 83.3 | 83.8 | 83.8 | 84.2 |
| A055   | -    | -    | 97.1 | 97.1 | 96.7 |
| A101   | -    | -    | -    | 96.3 | 96.7 |
| A136   | -    | -    | -    | -    | 98.0 |
| A182   | -    | -    | -    | -    | -    |

FIG. 1

SEQUENCE LISTING

<160> NUMBER OF SEQ ID NOS: 7

<210> SEQ ID NO 1
<211> LENGTH: 613
<212> TYPE: DNA
<213> ORGANISM: Foamy retrovirus

<400> SEQUENCE: 1

```
caatagatgg agtatttcct gttacaacac cagatctaag gtgcagaatt attaatgcta      60
tactaggagg aaacttaggg ttatcattaa ccccagcaga ctgtgtaaca tgggactctg     120
cagtaggcac actatttgta agaacccatg gacaatttcc aatgcatcag cttgggactg     180
taatacaagg aatagttaac caagaaggag tggcaacagc atatactttg ggaatgatgc     240
```

-continued

```
tttctggaca aaattatcca ttagtctcag gaattattcg gggatatttg cctggacaag    300
ctgtagtaac tgctttacaa cagcgcctag atcaagaagt agacgatcaa gcgcgagcag    360
aaacctttat tcaacatcta aatgctgtat atgaaatttt aggccttaat gccagaggac    420
agagtatacg tgcttcagtg actcctcagc cccgaccgtc tagaggtaga ggtcgaggcc    480
aaagtactcc tagaccctct caaggaccag ctagtagcgg acgtggacga cagcgtcctg    540
cttctggtca atacgacaga ggatctaata atcaaaatca aatcaagga aatacaagtc    600 aaggaggata taa                                                       613
```

<210> SEQ ID NO 2
<211> LENGTH: 616
<212> TYPE: DNA
<213> ORGANISM: Foamy retrovirus

<400> SEQUENCE: 2

```
cagcaataga tggagtattt cctgttacaa caccagatct aaggtgcaga attattaatg    60
ctatactagg aggaaactta gggttatcat taaccccagc agactgtgta acatgggact    120
ctgcagtagg cacactattt gtaagaaccc atggacaatt tccaatgcat cagcttggga    180
ctgtaataca aggaatagtt aaccaagaag gagtggcaac agcatatact ttgggaatga    240
tgctttctgg acaaaattat ccattagtct caggaattat tcggggatat ttgcctggac    300
aagctgtagt aactgcttta caacagcgcc tagatcaaga agtagacgat caagcgcgag    360 cagaaaacctt tattcaacat ctaaatgctg tatatgaaat tttaggcctt aatgccagag    420
gacagagtat acgtgcttca gtgactcctc agccccgacc gtctagaggt agaggtcgag    480
gccaaagtac tcctagaccc tctcaaggac cagctagtag cggacgtgga cgacagcgtc    540
ctgcttctgg tcaatacgac agaggatcta ataatcaaaa tcaaaatcaa ggaaatacaa    600
gtcaaggagg atataa                                                    616
```

<210> SEQ ID NO 3
<211> LENGTH: 425
<212> TYPE: DNA
<213> ORGANISM: Foamy retrovirus

<400> SEQUENCE: 3

```
aattattaca gggtcaaaat gtaaaaggat atcctaaaca atatacatac tttttagaag    60
atggcaaagt aaaagtttcc agacctgaag gggttaaagt tattccccca caatcagacc    120
gacaaaaaat agtgcttcaa gcccataatt tagcccacac cggacgtgaa gccactcttt    180
taaaaattgc caacctttac tggtggccaa atatgaggaa ggatgtggtt aaacaactag    240
gacgttgcca gcagtgttta atcacaaatg cttccaacaa agcctctggt cccatattaa    300
gaccagatag gcctcaaaag ccttttgata aattttttat tgattatatt ggaccttgc    360 caccttcaca aggatatctt tatgtattag ttgttgttga tggaatgaca ggatttacat    420
ggtta                                                                425
```

<210> SEQ ID NO 4
<211> LENGTH: 425
<212> TYPE: DNA
<213> ORGANISM: Foamy retrovirus

<400> SEQUENCE: 4

```
aattattaca gggtcaaaat gtaaaaggat atcctaaaca atatacatac tttttagaag    60
atggcaaagt aaaagtttcc agacctgaag gggttaaagt tattccccca caatcagacc    120
```

```
gacaaaaaat agtgcttcaa gcccataatt tagcccacac cggacgtgaa gccactcttt      180
taaaaattgc aaccttttac tggtggccaa atatgaggaa ggatgtggtt aaacaactag      240
gacgttgcca gcagtgttta atcacaaatg cttccaacaa agcctctggt cccatattaa      300
gaccagatag gcctcaaaag ccttttgata aatttttat tgattatatt ggacctttgc       360
caccttcaca aggatatctt tatgtattag ttgttgttga tggaatgaca ggatttacat      420
ggtta                                                                  425

<210> SEQ ID NO 5
<211> LENGTH: 240
<212> TYPE: DNA
<213> ORGANISM: Foamy retrovirus

<400> SEQUENCE: 5
ttatgtttta aagtaatcta tgaaggagct atgagtcaaa acaagaaca aaagagctgg       60 ctatgtagat taggacatgg ccatcgcatg ggggcttatg aatatcgcag aatagattta     120
tatgctatga aaaagggaaa agaaaacccc tatggagaaa ggggagatgt agctttgcaa     180
tatgcttatc aggttaaaag aggctgtaaa gcaggatgct agcttcaca agtgcttaac      240

<210> SEQ ID NO 6
<211> LENGTH: 240
<212> TYPE: DNA
<213> ORGANISM: Foamy retrovirus

<400> SEQUENCE: 6
ttatgtttta aagtaatcta tgaaggagcc atgggtcaaa acaagagca aaaaagctgg      60 ctatgcaggc taggacatgg ccaccgtatg ggtgcttatg actatcgcag agtagattta    120
tatgctatga aaaagggaaa agaaaacccc tatggagaaa ggggagatgt agctttgcaa    180
tatgcttatc aggttaaaag aggctgcaaa gcaggatgct agcttcacc agtgcttaat     240

<210> SEQ ID NO 7
<211> LENGTH: 3576
<212> TYPE: DNA
<213> ORGANISM: Foamy retrovirus

<400> SEQUENCE: 7
tatttacatc ttgaagactg cagaagacaa gattatgtca tatgtgatgt ggtaaagata     60
gtacagcctt gtggcaatag ctcagacacg agtgactgtc ctgtctgggc tgaggctgta   120
aaagaaccat tgtgcaagt gaatcctctg aaaaacggaa gttatctggt tttagcaagc    180
tccactgact gccagatccc accatatgtt cctagcattg tgactgttaa cgaaacaaca    240
tcgtgttatg gactggactt taaaaggcca ctagttgcgg aagaaagatt gagctttgag    300
ccacgactgc caaatctaca gctcagatta ccacatttgg taggaattat tgcaaaaatt    360
aaagggataa aaatagaagt tacatcctct ggagaaagta aaagaccaga ttgaaaga     420 gcaaaagctg agcttcttcg tctggacatc cacgaaggag atactcctgc ctggatacaa    480
caactcgctg cagcaacaag agccgtttgg ccagcagccg cctctgctct acaaggaatt   540
gggaactttc tatctggggc tgcccaagga atatttggaa ctgcctttag tattttggga   600
tatttaaagc ctatcctcat aggtgtgggg gtcattcttt tgatcattct tatatttaag   660
attgtatcat ggattcctac caagaagaag aatcagtagc ctccacctct ggcattcaga   720
acctgcagac tctagtgag cttgttggtc ctgaaaatgc tggagaggga gagctagtta    780
```

-continued

```
ttgctgaaga acctgaagaa aatcctcggc gtcctaaaag atacactaaa agagaagtta        840
aatgtgtatc ctaccatgcc tatagagaac ttgaggaaaa acatcctcaa cacatcaagc        900
tccaagactg gattcccaca cctgaagaaa tgagtaagtc actttgtaca agactaatct        960
tatgtggact atatagtgca gagaaggcag gggaaatatt acggatgcct tttacagtat       1020
cttgggaaca atcagacact gactctaaat gttttattgt gagttacaca tgtatattct       1080
gtgatgctat aatacatgac cctatgccca taatgtggga tcctgaggtc aagatatggg       1140
taaaatataa acccctcaga ggaattgttg gatctgctgt gtttatcatg cataaacatc       1200
aaagaaactg ttcttttgtt aaaccttcta ctagttactc agaaggtcca aaaccaagac       1260
ctaggcacga tcctgtcctt cgatgtgaca tgtttgaaaa gcatcacaag cctcgggaga       1320
aacgacccag gaaacgatcc atcgataatg agtcatgtgc ttccagtagt gacaccttgg       1380
ccaatgagcc aggatcacta tgcaccaacc ctctttggaa tcctggatca ctactacaag       1440
gagtgcttga agaatccagc aacttttcaa acttggaagt tcacatgtca ggtggaccct       1500
tctgggaaga ggtttatggg gactcaattt tgggtccccc ctctgggtca ggtgaacatt       1560
cagttttata aaaattacca aattttaact tgctgtcagg ctgtagatcc atttgctaat       1620
atctttcatg gtactgatga tgaaatgtat gatattgatt caggacctga tgtttggtgt       1680
acccctctt tatgttttaa agtaatctat gagggagcta ttggtcaaaa acaagaacaa       1740
aagagctggc tatgtagatt aggacatggc catcgcatgg gggcttatga atatcgcaga       1800
atagatttat atgctatgaa aaagggaaaa gaaaacccct atggagaaag gggagatgta       1860
gctttgcaat atgcttatca ggttaaaaga ggctgtaaag caggatgctt agcttcacaa       1920
gtgcttaact tcaaagctct gcagttccac agaacccctta tggctgacct caccaatcct       1980
agattggaga gggacatctt gcctcatggc tatcaggcag ctatggaagc ttatggacct       2040
cagagaggaa gtagcgagga gagggtgtgg tggaatgcca ctagaaatca aggaagagat       2100
ggggagtatt acagagaagg aggtgaagag cctcattatc cgaatactcc agcccctcat       2160
aaaaagacct gggatgaaag acataaggtc cttaagttgt cctcattcgc tactccctct       2220
gacatccaac gctgggctac cagagcactg ccatatggct ggaaagtagt tactgaggca       2280
ggggatgact atactagccg cagaaaaatc agaacgctga cagatatgac tcaggatgaa       2340
attagacaaa gatgggaaag gggatactgt gacccttca ttgactcagg aagtgactca       2400
gatggacccc tgtaaaagcc acaagcagta aaagtgtgtt aacactttag acagtattat       2460
atttgcttaa gcattaaaag ctttcatata ctcagtagct gtttcacaat caacaaaaca       2520
atgatgatgt aatcataagg aagtagttta aaataggtta agtaagttta ctgcagtaga       2580
taatccctgg ggaggatctg gctctgtaag ctggaacagc aatgttttca gttccagtcc       2640
tctcaaagga gaaccacagg gatgatgcgt tagttcgaat cccattatcc tcatggttcc       2700
cttttccaca ttttataatg taagttttag ggataagttt tatatgagct ttactaatcc       2760
ttgaaggaag aatagctctt caggtaaaga ggccagtatt aaaagagcta cccttccttt       2820
ttatataagg atcgaaacct gctttacgtt ttgctttaat gaagctaagt tttaagtttt       2880
aacaggaaat gctcttaggc agaaggtagc tccctcgact gggtgacaag aagaaaccat       2940
tcaggaagtg cttccttctg ctcggggaga tacatgagta tacagtagtt cgagtcctgt       3000
gtgctgatgt tgtcttctcg gctctttgt gacatcacaa atgtaaccta gaggtagtct       3060
tttaagaggt ttttacctca ggaaggagtg tggctaatac tggtaaggca cctaactatc       3120
agtacattta agtccattcc tccccatgtt ctcagggtgt gtgcggcgta agatcgaatc       3180
```

```
cccacacacc cgggaacttg cttattgcat aacgttttta ttagtcatat agaaaataat    3240
ataggataag agataggaat taaagcatga ggtgtgtggc tcaacacgta gagtgacaag    3300
gaactctact gtaataggac acaacacctc taaagttgcc cgtgggaagg tgaagtgaga    3360
tcgaatcttt ccttaacgca ggcagctttt tatccactag ggataatgtt ttaaggaata    3420
ttatagtaat agattgatag ctttaacaat gttagaaata gtatatagga ataagatgta    3480
gattgtacga gagctcctca ctactcgctg cgtcgagagt gtatgagact ctccaggttt    3540
ggtaagaata tttttattgt tattatgatc cattaa                              3576
```

ISOLATION OF A HUMAN RETROVIRUS

The present application is a 35 U.S.C. § 371 national phase application from, and claims priority to, international application PCT/US00/16433, filed Jun. 14, 2000 (published under PCT Article 21(2) in English), which claims priority to U.S. provisional patent application Ser. No. 60/139,219, filed Jun. 14,1999, which applications are incorporated herein in their entirety by reference.

This invention was made by the Centers for Disease Control and Prevention, an agency of the United States Government.

TECHNICAL FIELD

The present invention relates to a novel retrovirus, a spumavirus, that has been isolated from a human. More particularly, the novel spumavirus may be used as a vector for gene therapy or as a recombinant virus vaccine. The invention can also serve as a reagent in pathogenicity studies of related viruses and be used to screen for spumavirus infection in humans.

BACKGROUND OF THE INVENTION

Spumavirus, also known as foamy virus for the characteristics of vacuolization the virus induces in cell culture, belongs to a distinct group of retroviruses. The simian foamy viruses (SFVs) include isolates from Old World and New World monkeys and are classified into 10 different serotypes based on serological cross-reactivities. Virus appears to persist in the host for a long period of time in a latent form and can exist in the presence of neutralizing antibody.

Currently the most studied retrovirus, human immunodeficiency virus (HIV), is believed to be derived from non-human primate transmission into humans at some past time. Concerns about the risk of transmission of retroviruses from non-human primates (NHP) to humans working in research laboratories were heightened in the early 1990's when two persons developed antibodies to SIV (simian immunodeficiency virus) following work-related exposures, one of whom had clear evidence of persistent viral infection. (See CDC Anonymous survey for simian immunodeficiency virus (SIV) seropositivity in SIV laboratory researchers—United States, 1992. MMWR Morb. Mort. Wkly. Rep. 1992; 41: 814–5; Khabbaz R. F., et al. Brief report: infection of a laboratory worker with simian immunodeficiency virus. New Eng. J. Med. 1994; 330: 172–7; Khabbaz R. F., et al. Simian immunodeficiency virus needlestick accident in a laboratory worker. Lancet 1992; 340: 271–3; and CDC. Guideline to prevent simian immunodeficiency virus infection in laboratory workers and animal handlers. MMWR 1988; 37:693–704.) In addition to SIV, non-human primate species used in biomedical research are commonly infected with SFV (simian foamy virus), STLV (simian t-cell lymphotrophic virus), and/or type D retroviruses. All of these retroviruses cause lifelong infections in NHP, and some are known to be transmissible through sexual contact, blood, or breast feeding. Natural SFV infections in non-human primates have not been definitively associated with disease. In NHP, infection with the other retroviruses may result in a clinical spectrum ranging from asymptomatic infection to life threatening immunodeficiency syndromes or lymphoproliferative disorders. The transmission routes of SFVs among non-human primates remain undefined, but the prevalence of seroreactivity is high among captive adult non-human primates.

Studies of the prevalence of spumavirus infection of humans are limited and the findings are not definitive. Though there is some evidence of human infection with SFV (antibodies and positive PCR results), such occurrence has been reported in only two persons, both of whom had occupational risks for infection. Associated disease was not reported in either. (See Schweizer M., et al. Absence of foamy virus DNA in Graves' disease. AIDS Res. & Human Retrov. 1994; 10: 601–5; Neumann-Haefelin D., et al., Foamy viruses. Intervirology 1993; 35: 196–207; and Schweizer M., et al., Markers of foamy virus infections in monkeys, apes, and accidentally infected humans: appropriate testing fails to confirm suspected foamy virus prevalence in humans. AIDS Res. & Human Retrov. 1995; 11: 161–70).

Other inconclusive evidence was seen in early studies which described a relatively high rate of seroreactivity to antibodies to spumaviruses among human populations not known to be exposed to non-human primates. In some instances seroreactivity was suggestively linked to human disease, including disorders of the central nervous system, thyroid disease, and Chronic Fatigue Syndrome. In most instances these studies lacked definitive evidence of human infection and were not subsequently confirmed (See Heneine, W., et al., Absence of evidence for human spumaretrovirus sequences in patients with Graves' disease [letter]. J. Acq. Immune Defic. Synd. & Human Retrov. 1995; 9: 99–101; Simonsen, L., et al.,. Absence of evidence for infection with the human spumaretrovirus in an outbreak of Meniere-like vertiginous illness in Wyoming, USA [letter]. Acta Oto-Laryngologica 1994; 114: 223–4; and Heneine, W., et al., Lack of evidence for infection with known human and animal retroviruses in patients with chronic fatigue syndrome. Clin. Infect. Dis. 1994; 18: S121–5).

Recent publications indicate that earlier serological tests showing human spumavirus antibodies in the human population were incorrect. Immunological investigation of a previously reported human spumavirus revealed that it shared common antigens in complement fixation, immunofluorescence and neutralization assays with the chimpanzee foamy virus, SFV-6. The virus known as HFV, Human Foamy Virus was derived from a nasocarcinoma and is now believed not to be a human foamy virus, but a chimpanzee virus. Failure to detect serological evidence of HFV infection in people from a wide geographical area suggested that this virus isolate was a variant of SFV-6, particularly since sera from chimpanzees naturally infected with SFV-6 neutralized both viruses. In a survey for prevalence of HFV in more than 5000 human sera, collected from geographically diverse populations, none of the serum samples were confirmed as positive. Taken together with sequence analysis endorsing the phylogenetic closeness of the purported human spumavirus to SFV-6, these data strongly suggest that HIV is not naturally found in the human population. (See AH, M. et al., "No evidence of antibody to Human Foamy Virus in widespread human populations," AIDS Research and Human Retroviruses, Vol. 12, No. 15, 1996).

Novel human spumaviruses have been found in humans who were exposed to nonhuman primates. These novel viruses are unique viruses that reproduce in humans and yet cause no disease. These viruses are disclosed in U.S. Pat. No. 5,882,912 and U.S. patent application Ser. No. 60/105, 811, incorporated in their entirety herein. The existence of new human retroviruses in humans that were derived originally from simian sources indicates a need for compositions and methods for the immunological screening of the human population for the prevalence of spumavirus infection as web as for the screening of the human blood supply.

Recent concern that xenotransplantation, the use of living tissues from nonhuman species in humans for medical purposes, may introduce new infections into the human community has increased the importance of defining the ability of simian retroviruses to infect and/or cause disease in humans (See Chapman, L. E., et al. Xenotransplantation and xenogeneic infections. New Engl. J. Med. 1995; 333: 1498–1501; DHHS. Docket No. 96M0311. Draft Public Health Service (PHS) Guideline on Infectious

BRIEF DESCRIPTION OF THE DRAWINGS

FIG. 1 is a DNA sequence comparison between SFVHu-6 and various simian viruses isolated from chimpanzee subspecies. The numbers indicate percent identity between SFVHu-6 and the viruses isolated from individual chimpanzees, source chimp B1, and other chimps the exposed person worked with, A055, A101, A136 and A182 within the integrase, gag and ORF2 gene regions.

DETAILED DESCRIPTION OF THE INVENTION

Figure 2A:
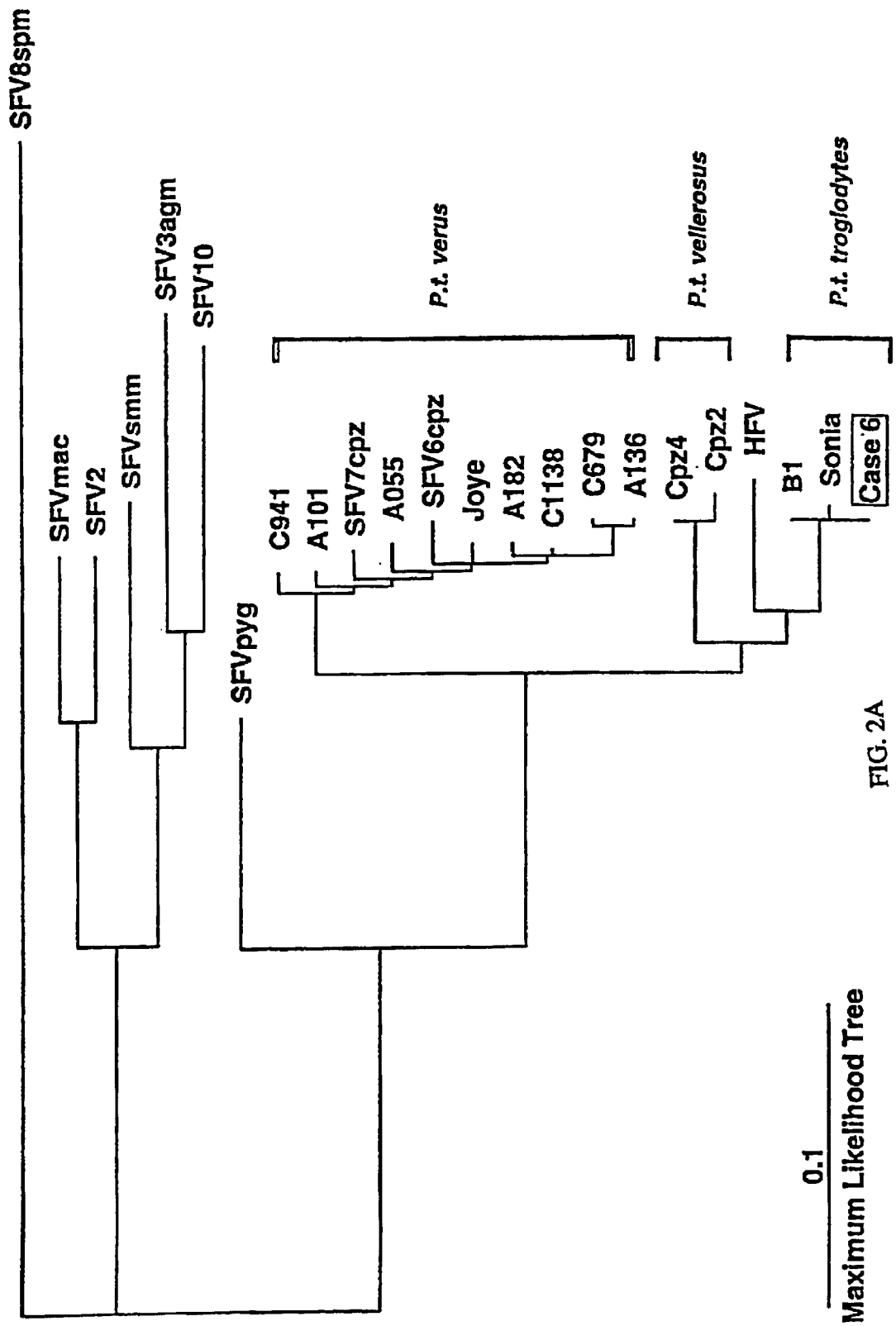
FIG. 2 (a and b) are phylogenetic trees showing the relationships between the integrase gene sequence of the novel spumavirus of the present invention and known spumaviruses from other non-human primates and various chimpanzee subspecies, including the source chimp, B1.

The present invention is directed to methods and compositions comprising a novel spumavirus, SFVHu-6. The novel spumavirus of the present invention has multiple utilities, in part, based on its characteristics of an inability to cause disease in the infected human and its inability to transfer between an infected human and close contacts of the human. Some of these utilities include use of compositions derived from the human spumavirus as a reagent for the immunological screening for spumaviruses in humans, especially those who work with nonhuman primates (NHP), as well as spumavirus infection in general. The novel spumavirus of the present invention can also serve as a vector in gene therapy because the virus appears to cause no disease in humans and is not transmitted to other humans. The novel spumavirus is a useful candidate as a gene therapy vector. Additionally, the novel spumavirus of the present invention can be used as a reagent in pathogenicity studies of these and other related viruses. Moreover, the sequences of SFVHu-6 of the present invention can be used as probes to detect virus or antibodies to the virus in biological samples. Vectors include, but are not limited to, procaryotic, eucaryotic and viral vectors. The spumavirus of the present invention can also be used as a live recombinant virus vaccine. Additionally, the spumavirus of the present invention can be used as a replicating viral system to kill live dividing cells, either in vitro or in vivo.

The spumaviruses or foamy viruses are by far the least well characterized of the retroviruses. They have been isolated as agents that cause vacuolation ("foaming") of cells in culture from a number of in vitro. The present invention comprises methods and compositions comprising recombinant live virus vaccines using SFVHu-6 as the viral vector. The present invention also comprises methods and compositions for detecting spumavirus or antibodies to spumavirus in biological fluids, tissues or organs.

Accordingly, it is an object of the present invention to provide compositions comprising a novel spumavirus.

It is another object of the present invention to provide methods of detecting a spumavirus.

It is yet another object of the present invention to provide methods and compositions for detecting the presence and amount of spumavirus in a body fluid or organ.

A further object of the present invention is to provide compositions and methods for treating genetic and physiologic disorders using gene therapy techniques comprising the novel spumavirus of the present invention as a vector for nucleic acid sequences and antisense sequences.

Another object of the present invention is to provide compositions and methods useful for manipulating the expression of genes.

Yet another object of the invention is to provide vaccines.

Still a further object of the present invention is to provide compositions and methods for treating viral infections in humans or animals.

Another object of the present invention is to provide compositions and methods that are effective in treating genetic diseases.

An object of the present invention is to provide methods of treating microbial infections in humans or animals.

It is another object of the present invention to provide for treatments of conditions that are caused in part by rapidly dividing cellular growth.

Another object of the present invention is to provide live recombinant virus vaccines.

An object of the present invention is to provide diagnostic tools such as antibodies or antigens for the monitoring of the blood supply or organ and tissue donation for the presence of spumavirus.

An object of the present invention is to provide reagents for pathogenecity studies.

These and other features and advantages of the present invention will become apparent after a review of the following detailed description of the disclosed embodiments and the appended claims.

Disease Issues in Xenotransplantation. Federal Register Vol. 61, No. 185. Sep. 23, 1996). Currently, the primary animal species considered as donors for xenografts are baboons and pigs, though other species may be considered in the future. Thus, what is needed are compositions and methods for detecting viruses that may be transmitted from the nonhuman organ donors to the recipient human. Additionally, information regarding these transmissible agents may provide valuable information about the organ donors' cellular receptors that may be important for transplantation success.

Gene therapies have long looked for a good vector that can transport the foreign gene of choice into human cells. The lack of any known disease associated with the virus of the present invention makes the present invention an ideal candidate for gene therapy regimens. Thus, compositions and methods for gene therapy are needed that use a vector capable of carrying a significant amount of foreign DNA that will enter the host organism and not cause disease.

Compositions and methods for vaccination using recombinant live retroviruses are also needed. A live virus, that causes no illness in humans, and that has genes of antigens of choice incorporated into its genome, would provide for an excellent vaccination tool. The retrovirus would reproduce in the human host and expose the immune system to antigens so that an immune response can be initiated.

Targeted attack on reproducing cells is a goal of cancer treatment. What is needed are compositions and methods for cancer treatment that are specific for dividing cells that do not cause systemic damage to the cancer patient. A virus that could infect and kill dividing cells, without killing other cells of the host would provide a solution for cancer treatment.

SUMMARY OF THE INVENTION

The present invention is directed to methods and compositions comprising a novel spumavirus or foamy virus, taxonomically named SFVHu-6. The virus was deposited with the American Type Culture Collection (ATCC) on Dec. 2, 1998. The present invention comprises an isolated human spumavirus that has been definitively derived from a human with no disease. The novel spumavirus of the present invention has been maintained through tissue culture cells where it causes the vacuolation of the cells that is characteristic of foamy viruses.

The present invention further comprises methods and compositions for the use of a replicating viral system to kill live dividing cells in a host or mammalian species, including monkeys, cattle, cats, and reportedly in humans. Persistent infection with these viruses is not associated with any known disease.

Recent studies using improved diagnostic assays have shown no evidence of human foamy virus infection of humans in studies of large populations (approximately 8,000 persons). Given these results, the identification of seroreactivity in six persons occupationally exposed to non-human primates is notable and several different novel spumaviruses have been isolated from such workers.

Two of these human spumaviruses, SFVHu-1 and SFVHu-3, disclosed in U.S. Pat. No. 5,882,912 and PCT/US99/25171, incorporated herein in their entirety, were isolated from two occupationally exposed workers. SFVHu-1 has structural and functional similarities to a simian spumavirus of African green monkey origin while SFVHu-3 has similarities with a baboon-like simian spumavirus.

The present invention comprises the isolation and characterization of a spumavirus, SFVHu-6, that was shown to have been transmitted from a non-human primate to a human at some point in the past. The retrovirus of the present invention, unlike another retrovirus of a more virulent nature, HIV-1 (human immunodeficiency virus-type 1), is not readily transmitted from human to human. The spumavirus of the present invention can be used in diagnosing spumavirus infections and used as a vector in gene therapy procedures.

The present invention also includes methods and compositions for detecting spumavirus in biological fluids. The methods and compositions, including kits, can be in any configuration well known to those of ordinary skill in the art. The present invention also includes antibodies specific for the spumavirus and antibodies that inhibit the binding of antibodies specific for the spumavirus. These antibodies can be polyclonal antibodies or monoclonal antibodies, or fragments thereof. The antibodies specific for the spumavirus can be used in diagnostic kits to detect the presence and quantity of spumavirus in biological fluids or in organs from non-human primates for xenotransplantation. Antibodies specific for spumavirus may also be administered to a human or animal to passively immunize the human or animal against spumavirus, thereby reducing infection after accidental exposure to non-human primate bodily fluids.

The present invention also includes compositions and methods, including kits, for detecting the presence and quantity of antibodies that bind spumavirus in body fluids. The methods, including kits, can be in any configuration well known to those of ordinary skill in the art Such kits for detection of spumavirus itself or detection of antibodies to the spumavirus can be used to monitor the blood supply for the presence of spumavirus in the blood supply.

The present invention also includes methods and compositions comprising recombinant live virus vaccines. Exogenous genes can be inserted into the genome of the virus of the present invention. The genes can code for any protein or proteins for which vaccination or gene therapy is desired. SFVHu-6 can provide a high level of antigen to the host carrying the virus. As an example of such use, SFVHu-6 carrying exogenous genes is administered to a human, the virus would infect the cells and replicate. The exogenous genes would be translated and would provide the selected antigens to the immune system of the human. A novel aspect of such recombinant live viruses is that SFVHu-6 does not cause disease in the human. Additionally, there is no transmission from one human to another non-infected human, even by close contact with exchange of bodily fluids. The recombinant live virus vaccines of the present invention provide one or several antigens in a most optimum method to the immune system of the selected human.

The present invention further includes methods and compositions for the use of a replicating viral system to kill live dividing cells in a host or in vitro. In in vitro uses, SFVHu-6 can be used to detect and kill rapidly dividing cells. Foamy viruses, including SFVHu-6, can infect a wide variety of species of cells and can be used in many in vitro cell systems. For example, if the assay of the in vitro cell system required the identification of quiescent cells, application of SFVHu-6 to the tissue culture system would result in the selection of the rapidly dividing cells by SFVHu-6. All of the tissue culture cells would be infected but only the dividing cells would be destroyed because SFVHu-6 has a productive infection and its cytopathic destruction effects only dividing cells. The remaining non-dividing cells of the culture would remain alive.

In a host, the ability of SFVHu-6 to infect dividing cells provides an excellent tent for conditions due to the presence of rapidly dividing cells. For example, a person with disease due to rapidly dividing cells, such as cancer or any known angiogenic condition such as angiogenesis-dependent diseases, could be infected with SFVHu-6. Such virus may or may not carry other, exogenous genes for other effects in the host. Because SFVHu-6 does not cause disease in humans and there is no transmission of the virus to close contacts with humans, only the person with the disease due to rapidly dividing cells will be treated. The virus will infect the rapidly dividing cells and kill them. For example, a person with a fast growing tumor would be infected with SFVHu-6 and the cells of the tumor would be destroyed by the virus. The SFVHu-6 can be recombinantly modified, for example, to be selective for cellular receptors on the tumor to make the virus even more specifically targeted to just those cells.

Such treatment with SFVHu-6 could be used for any condition in which rapidly dividing cells provide an aspect of the pathology of the condition. One such condition is the presence of uncontrolled angiogenesis within the body. Angiogenesis-dependent diseases are well known in the art and are caused in part by the rapid growth of blood vessels.

In response to the identification of simian immunodeficiency virus (SIV) infection in persons who work with simians, or other occupationally exposed workers, Centers for Disease Control and National Institutes for Health collaborated in an anonymous serosurvey of persons with similar work exposures. Simian immunodeficiency virus seroreactivity was present in 3/427 (0.7%) stored serum samples from these anonymous workers (See CDC, Anonymous survey for simian immunodeficiency virus (SIV) seropositivity in SIV laboratory researchers—United States, 1992. MMWR, Morb. Mort. Wkly. Rep. 1992; 41: 814–5; Khabbaz R. F., et al.,. Brief report: infection of a laboratory worker with simian immunodeficiency virus. New Eng. J. Med. 1994; 330: 172–7). Consequently, a voluntary testing and counseling program was developed that allowed linkage between specific exposures or health outcomes and serostatus of persons occupationally exposed to simian immunodeficiency virus. The workers enrolled in this voluntary, limp prospective simian immunodeficiency virus surveillance are also at occupational risk for exposure to other retroviruses common in NHP.

In 1995, the linked surveillance was expanded to include voluntary testing and counseling for exposure to simian spumaviruses (more commonly called simian foamy viruses, or SFV), simian T-lymphotropic viruses (STLV), and simian type D retroviruses (STRV). 1,823 samples from 13 institutions in the United States had been tested for simian immunodeficiency virus; samples from 231 of the participating volunteer workers were also tested for other retroviruses from non-human primates. Four of these 231 workers (1.7%) were determined to be infected with a SFV-hike virus by serology and PCR.

A seroprevalence of 3% (4/133) was found by Western blot analysis of zoo workers exposed to mammals including NHP. None of 189 unexposed zoo workers was SFV-positive Workers occupationally exposed to NHP in zoos or prima research are at risk of SFV zoonosis, primarily from chimpanzees, and thus represent a unique population to study the pathogenetic potential and transmissibility of zoonotic SFV infections.

An immunofluorescent assay that was developed using cells infected with a chimpanzee foamy virus, SFV-6cpz, identified antibodies to a SFV- like virus in recently collected serum specimens from a worker (Case 6). The specimens were also Western blot positive, showing reactivity to both p70 and p74 gag precursor bands of SFV-6cpz antigen. Repeat testing of additional sera obtained from this worker at later time points are also positive in both assays.

Additional blood samples from Case 6 were tested for SFV proviral DNA sequences using polymerase chain reaction (PCR) assays employing primer sets from two regions of the polymerase gene that are conserved among known primate foamy viruses. All samples were PCR positive in both regions. The PCR products from three regions (the gag, integrase and ORF2 gene) were sequenced. There was 93–100% identity between the virus sequences determined from the SFV-infected source chimp (SEQ ID 2, 4, 6) and the virus sequences determined from the human, Case 6, SFCHu-6 (SEQ ID 1, 3, 5). This near sequence identity confirms that the virus originated in chimpanzee B1 and was transmitted to Case 6. The corresponding RNA sequences and resulting proteins can be deduced from these sequences, and are included within the scope of the present invention.

SEQ. ID 1 comprises 613 nucleotides of the gag gene of SFVHu-6, SEQ ID 3 comprises 425 nucleotides of the int (integrase) gene of SFVHu-6, and SEQ ID 5 comprises 240 nucleotides of the ORF 2 of SFVHu-6. SEQ ID 7 comprises the 3' part of the env (envelope) gene, the complete ORF1 and ORF2 and the 5' end of the 3' LTR of SFVHu-6. SEQ. ID 2 comprises 616 nucleotides of the gag gene of the virus isolate from B1, SEQ. ID 4 comprises 425 nucleotides of the integrase gene of the virus isolate from B1, and SEQ. ID 6 comprises 240 nucleotides of the ORF2 of the virus isolate from B1.

Case 6 was severely bitten by chimpanzee B1 in 1977. Chimpanzee B1 is currently in good health. A serum sample obtained from chimpanzee B1 was found to be positive for SFV-6antibodies. SFV-6sequences from the peripheral blood lymphocytes (PBL) of B1 and from four other SFV-infected chimpanzees from the same facility were amplified and compared to Case 6. Sequences from Case 6 and chimpanzee B1 were indistinguishable (100% identity) in both the integrase and gag regions. In contrast, the SFV integrase and gag sequences from the four control chimpanzees were 92.7 to 93.6% and 84.4 and 84.7% homologous to those of Case 6, respectively. See FIG. 1 for a chart of the comparison. The observed identity in the SFV-6sequences reflects the high genetic stability of SFV-6, a characteristic seen in human/simian T lymphotrophic viruses rather than in HIV/SIV infections. This genetic stability makes the present invention uniquely well suited for gene therapy uses.

Figure 2B:
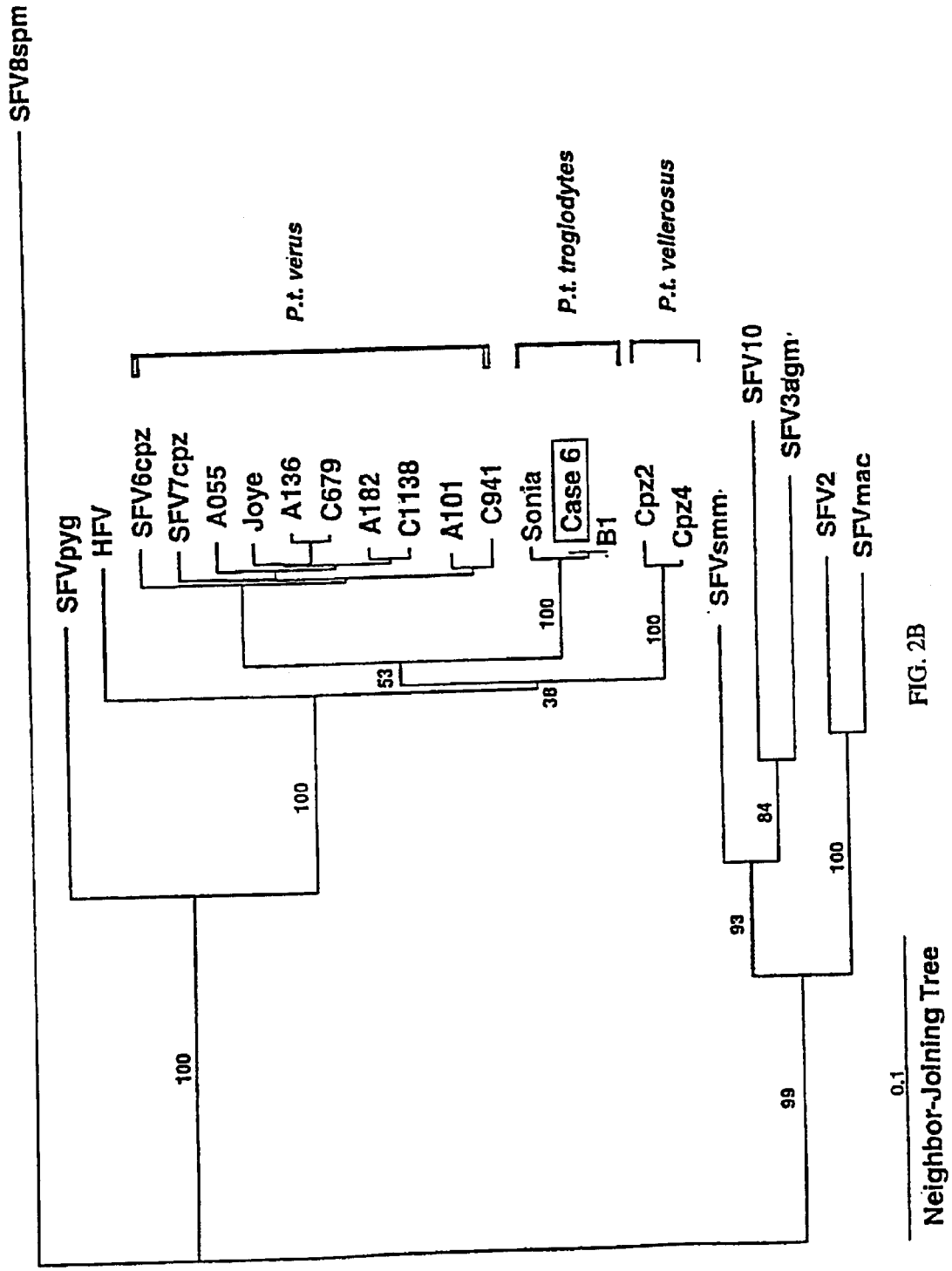

The discovery of subspecies-specific diversity in SIV from chimpanzees (SIVcpz) raised the possibility that a similar evolution of SFV in chimpanzee subspecies might explain the sequence difference between Case 6 and the control chimpanzees. Thus, the subspecies of all live chimpanzees was determined by mitochondrial DNA analysis. B1 was found to be *Pan troglodytes* troglodytes (*P. t. troglodytes*) while the other four control chimpanzees, infected with the closely related SFV, belonged to *Pan troglodytes verus* (*P. t. verus*). The relationship between the SFVHu-6 isolate and other known spumaviruses is shown in FIG. 2 (a and b) which is a phylogenetic tree based on the homology of the nucleotide sequences of these viruses. Phylogenetic analysis using the integrase sequences clearly indicates that the sequence pair from Case 6 and chimpanzee B1 fell within the clade of chimpanzee sequences but did not cluster with any other sequences including those from the four control chimpanzees. Thus, the source of the SFV in Case 6 is chimpanzee B1. The identification of this primary zoonotic SFV infection provides a unique opportunity to study the early events of retrovirus adaptation to the human host.

Case 6 provides a rare opportunity to examine SFV genome stability during both zoonotic transmission and persistent human infection. SFV endemic to different species of non-human primates demonstrates the greatest level of genome sequence diversity within the U3 region of the long terminal repeat (LTR) and the 3' accessory open-reading frames (ORF), suggesting that adaptive changes may occur during zoonosis. In foamy viruses, the LTR aids in the replication of the virus. The LTR is transactivated by a virus-specific protein, and unlike a related retrovirus, HIV, no human cellular transcription factors activate the virus. LTRs in retroviruses like HIV have conserved consensus sequences for cellular transcription factors.

It is known that another human-derived spumavirus has stable, conserved LTRs and internal promoters, providing conserved transcriptionally important regions in such viruses. The sequence analysis shown in FIG. 1 indicates that there is little genetic variation that occurs during cross species transmission of SFV to humans. Thus, for gene therapy uses, this stability indicates that the virus is not acquiring human sequences that would cause it to possibly become virulent or at least cause disease in humans due to introduced mutations. With such conserved regions, SFVHu-6, is an excellent vector, vaccine or gene therapy agent for humans. This stability is surprising in light of the high instability of the LTR of the virus known as HFV (Human Foamy Virus). HFV was derived from a nasocarcinoma and is now believed not to be a human foamy virus, but a chimpanzee virus. The HFV LTR is unstable and has many deletions, thus making it an undesirable vector.

To date, zoonotic transmission of NHP retroviruses to humans has only been substantiated by indirect evidence such as phylogentic relatedness between NHP and human retroviruses. The present invention is the first en direct evidence for a chimpanzee to-man retroviral zoonosis. To determine the species origin of SFVHu-6, two PBL-derived FV sequences were compared with prototype SFV sequences from different non-human primate species. These sequences represent conserved (integrase) or variable (gag) genomic regions among SFV . The results indicated that both sequences had the highest homology to SFV from chimpanzees (approximately 93% and 85% for the integrase and gag sequences respectively). Thus the foamy virus infection in Case 6 is of chimpanzee origin.

Figure 3:
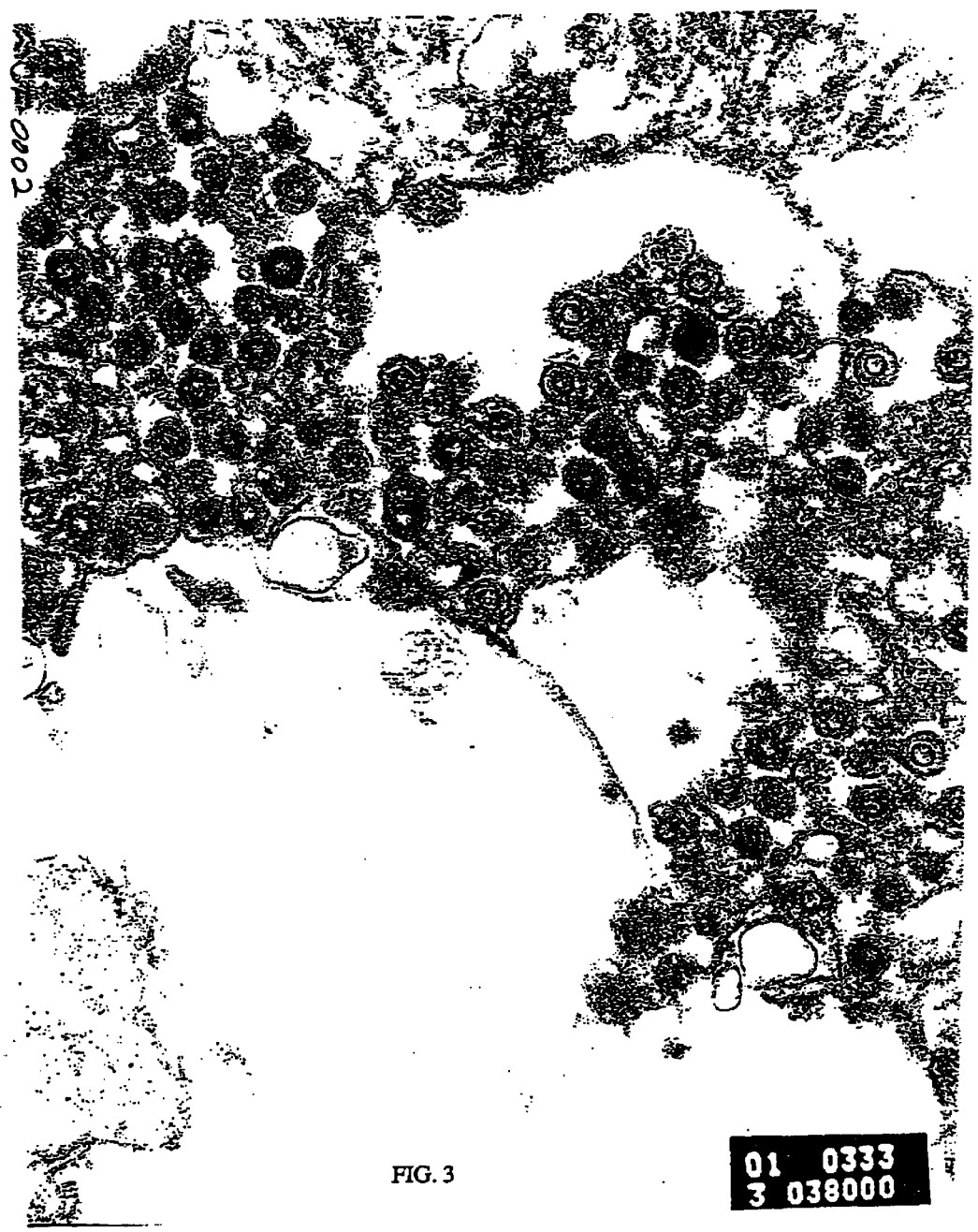
FIG. 3 shows an electron micrograph of the spumavirus isolated from Case 6, SFVHu-6.

SFVHu-6 is found in the PBL of the host and is cultured from such cells in tissue culture systems. Reverse transcriptase activity has been found in the PBL and plasma of the infected host. Virus isolation of SFVHu-6 was accomplished by co-culturing the PBL of the person identified as Case 6 with Canine thymocyte (Cf2th) cells. Importantly, this isolation has identified a cell line that is a susceptible host cell line for isolating SFVHu-6 and other chimpanzee-like spumaviruses. Reverse transcriptase activity was detected in co-cultures from the cells exposed to Case 6 PBLs but not from controls. Transfer of supernatant from the above cells exposed to Case 6's PBL passed this reverse transcriptase activity to uninfected cells, which subsequently showed cytopathic effect (CPE). This finding indicated that the infectious agent in Case 6's PBL was transmitted to tissue culture cells which were used to transfer the infectious agent into other tissue culture cells. Additionally, this indicated that the infectious agent reproduced in the Canine thymocyte (Cf2th) cells. DNA-PCR of infected cells was found to be positive for a SFV-like virus. Infected cells showed strong reactivity with Case 6's sera by both immunofluorescent assay and Western blot and no reactivity with normal sera controls. By electron microscopy, infected Canine thymocyte (Cf2th) cells, derived from cell free supernatants from cells infected by exposure to infected PBL, showed a morphology characteristic of foamy virus infection (See FIG. 3).

Th present invention is directed to compositions and methods comprising a new spumavirus, SFVHu-6. The virus was isolated from a human who had a severe injury from interaction with a chimpanzee, along with exposure to many other non-human primates. The new spumavirus, or foamy virus, does not appear to cause any disease in human hosts. The new virus of the present invention is an excellent vector for gene therapy and for vaccination purposes. Additionally, the antibodies or other detection methods for detecting the new virus can be used to detect the presence of this and related viruses. In addition, the novel spumavirus of the present invention can be used as a reagent in pathogenicity studies of these and related viruses. Moreover, the sequences of the novel spumavirus of the present invention can be used as probes to detect virus in biological samples. Vectors include but are not limited to procaryotic, eucaryotic and viral vectors.

The sequences of SEQ ID 1–6 can be used for all the molecular biological techniques known to those skilled in the art. Such uses include, but are not limited to, generation of probes and vectors containing the sequences, antisense sequences derived from such sequences, RNA sequences such as antisense RNA, ribozyme RNA, decoy RNA, and proteins synthesized using the sequences. RNA and other nucleic acid derivatives are contemplated by the present invention. Spumaviruses can tolerate large deletions and still remain infectious. Such deletion sites can be used as the sites of insertion of exogenous sequences that are contemplated by the present invention. Additionally, exogenous sequences may be inserted without deletions.

Many new and potentially useful technologies are being developed which use viral vectors and may form the basis of future medical cures and therapies. Examples of such technologies include, but are not limited to, gene replacement, antisense gene therapy, in situ drug delivery, treatment of cancer or infectious agents, and vaccine therapy. However, to be successful, these technologies require an effective means for the delivery of the genetic information across cellular membranes. SFVHu-6 can function as a vector to carry such genes when infecting cells.

The recent advent of technology, and advances in the understanding of the structure and function of many genes makes it possible to selectively turn off or modify the activity of a given gene. Alteration of gene activity can be accomplished many ways. For example, oligonucleotides that are complementary to certain gene messages or vial sequences, known as "antisense" compounds, have been shown to have an inhibitory effect against viruses. By creating an antisense compound that hybridizes with the targeted RNA message of cells or viruses the translation of the message into protein can be interrupted or prevented. In this fashion, gene activity can be modulated.

The ability to deactivate specific genes provides great therapeutic benefits. For example, it is theoretically possible to fight viral diseases with antisense molecules that seek out and destroy viral gene products. In tissue culture, antisense oligonucleotides have inhibited infections by herpesviruses, influenza virus and the human immunodeficiency virus that causes AIDS. It may also be possible to target antisense oligonucleotides against mutated oncogenes. Antisense technology also holds the potential for regulating growth and development. However, in order for the gene therapy to work, antisense sequences must be delivered across cellular plasma membranes to the cytosol.

Gene activity is also modified using sense DNA in a technique known as gene therapy. Defective genes are replaced or supplemented by the administration of "good" or normal genes that are not subject to the defect. Instead of being defective, the genes have been deleted, thus replacement therapy would provide a copy of the gene for use by the cell. The administered normal genes can either insert into a chromosome or may be present as extracellular DNA and can be used to produce normal RNA, leading to production of the normal gene product. In this fashion gene defects and deficiencies in the production of a gene product may be corrected.

Still further gene therapy has the potential to augment the normal genetic complement of a cell. For example, it has been proposed that one way to combat HIV is to introduce into an infected person's T cells a gene that makes the cells resistant to HIV infection. This form of gene therapy is sometimes called "intracellular immunization." Genetic material such as a polynucleotide sequence may be administered to a mammal in a viral vector to elicit an immune response against the gene product of the administered nucleic acid sequence. Such gene vaccines elicit an immune response in the following manner. First, the vial vector containing the nucleic acid sequence is administered to a human or animal. Next, the administered sequence is expressed to form a gene product within the human or animal. The gene product inside the human or animal is recognized as foreign material and the immune system of the human or animal mounts an immunological response against the gene product. The virus of the present invention may be used as a viral vector to provide the foreign nucleic acid sequences to the intracellular metabolic processes.

Additionally, gene therapy may be used as a method of delivering drugs in vivo. For example, if genes that code for therapeutic compounds can be delivered to endothelial cells, the gene products would have facilitated access to the blood stream. Additionally, cells could be infected with a retroviral vector such as the present invention carrying nucleic acid sequences coding for pharmaceutical agents that prevent infection from occurring in the retrovirally infected cells.

The novel spumavirus of the present invention can also be used as a safe and effective vaccine agent. Exogenous genetic sequences for immunogenic proteins or polypeptides or antigenic fragments from a variety of infectious agents can be incorporated into the foamy virus RNA (the genome of the virus). Once inside a cell, the gene product is expressed and releases the immunizing peptide to the body's immune system. In another method, the virus of the present invention can be used to immunize the body against cell markers found on cancer or tumor cells. The genetic sequence of the cancer cell marker is incorporated into the foamy virus nucleic acids and after infection with the virus, the expressed gene product stimulates the immune system. The patient's immune system is used to remove the cancerous cells, obviating the need for chemotherapeutic methods.

The nucleic acid sequences of the virus of the present invention, SEQ ID 1–7, can be used in a variety of methods, including, but not limited to, PCR assays. Additionally, the sequences can be used to easily detect the presence of chimpanzee-like spumaviruses, similar to SFVHu-6, in organs, tissues or cells. The sequences can also be used to test for transmission of spumaviruses in animals who are in contact with non-human primates. For example, zoo workers show the greatest inactivity to antigens from chimpanzee foamy virus (FIG. 3). Thus these zoo workers and other animal care workers in non-human primates centers can be tested routinely for exposure to spumaviruses from various non-human primates. This facilitates comprehensive pathogenecity studies in which the workers could be tested for the transmission of viruses from the animals cared for by the caretaker. Thus, the invention can serve as both a reagent in pathogenicity studies of related viruses and be used to screen for spumavirus infection in humans.

The antibodies of the present invention can be used to detect the presence of the virus or viral particles of the present invention in body fluids or tissues. These antibodies can be raised in classical ways, such as immunination of animals with virus proteins, to generate antibodies, or through development of monoclonal antibodies using immunological or molecular biological techniques. These antibodies or antibody fragments can be used in diagnostic or screening kits to assess the presence of the virus, for example, in clinical specimens. Additionally, the antibodies can be used to screen organs from non-human primates that may be used in humans. Detection of the presence of a virus that is transmitted from non-human primates to humans would be crucial in providing virus-free organs for transplantation.

Additionally, the ability to screen for the presence of virus or antibody to virus in animal care workers will provide methods for monitoring the viral status of such workers. If an animal care worker is exposed to the animal's bodily fluids, and viral transmission is possible, then the antibodies of the present invention can be used to passively immunize such workers.

The virus of the present invention can be used for the treatment of conditions due to the presence of rapidly dividing cells. In a host, the ability of SFVHu-6 to productively infect dividing cells provides an excellent treatment for conditions due to the presence of rapidly dividing cells. For example, a person with disease due to rapidly dividing cells, including but not limited to cancer or any known angiogenic condition, could be infected with SFVHu-6. Such virus may or may not carry other exogenous genes for other effects in the host. Because SFVHu-6 does not cause disease in the host and there is no transmission of the virus to contacts with the host, only the person with the condition due to rapidly dividing cells win be treated. In addition, only the rapidly dividing cells of that host person will be productively infected by SFVHu-6. Other cells in the body may be infected but will not be killed because the infection in non-dividing cells is not productive. The virus will productively infect the rapidly dividing cells and kill them. For example, a person with a fast growing tumor would be infected with SFVHu-6 and the cells of the tumor would be destroyed by the virus. Additionally, the virus may be given to a person prior to the person developing a condition caused by dividing cells, and when the cells begin dividing, the virus would then undergo a productive infection and kill the cells. This therapy may halt or inhibit such conditions as leukemia or angiogenesis dependent diseases such as macular degeneration.

Such treatment with SFVHu-6 could be used for any condition in which rapidly dividing cells provide an aspect of the pathology of the condition. One such condition is the presence of uncontrolled angiogenesis within the body. Angiogenesis dependent diseases are well known in the art and are caused in part by the rapid growth of blood vessels. Another such condition is cancer or tumor growth. Cancer or tumors include both solid tumors and other types. Infection with the virus of the present invention, which causes no disease and does not effect the host systemically, is an improvement over currently known treatments that involved systemically administered agents. Such chemotherapeutic agents kill rapidly dividing cells but also cause trauma to the entire person.

In contrasts, treatments of cancer with the present invention are not as harmful to the patient. Unlike HFV, the present invention was not derived from a patient suffering from a carcinoma and thus does not pose a danger to the patient. The virus can either be administered systemically or injected in situ into the tumor. The virus will only replicate in rapidly dividing cells and will not effect cells that are not dividing. The infected cells are killed and tumor growth is stopped. The virus may be administered in one treatment or in a series of treatments.

The SFVHu-6 of the present invention can be recombinantly modified to be selective for cellular receptors on the tumor to make the virus even more specifically targeted to just those cells. Additionally, the virus may have altered promoter regions that can be selectively activated to cause a productive infection. The combination of different levels of control of the virus, both natural and recombinantly produced, are contemplated in the present invention. A virus could be made specific for attachment to only certain types of cellular receptors, for those cells that are dividing, and will only undergo replication if another exogenous promoter factor is present. Viral infection by two or more individually defective viruses, that require factors or promoters supplied by other foamy viruses or any type of virus, could provide for many levels of control of infection or treatment of specific conditions.

The virus may be administered to the host, for cancer treatment, gene therapy or vaccination by any methods known to those skilled in the art. Such methods include but arm not limited to injection, inhalation, ingestion, topical administration and implantation. The virus may be killed or live, depending on the treatment considered. In vitro uses of the virus, sequences, vectors or probes are contemplated by the present invention.

The virus of the present invention does not cause disease and does not appear to be transmitted by close household contacts or sexual contacts. This belief is supported by the epidemiology data, the PCR and sequencing data, and the serology data. The isolate from Case 6, SFVHu-6, was deposited with the ATCC, under the Budapest Treaty on Dec. 2, 1998, and was assigned ATCC No. VR-2635.

The present invention is further described by the examples which follow. Such examples, however, are not to be construed as limiting in any way either the spirit or scope of the present invention. In the examples, all parts are parts by weight unless stated otherwise.

EXAMPLES

Example 1

Peripheral blood lymphocytes (PBLs) were isolated from Case 6 and were cultured with IL-2 for 48 hours, in RPMI media with 10% fetal calf serum, and pen-strep antibiotics. After 48 hours, the PBLs were added to the Canine thymocyte (Cf2th) cells and co-cultured for 2–4 weeks. The cells were in DMEM supplemented with 2% non-essential amino acids, 20% fetal calf serum and pen-strep antibiotics. 1 mL supernatants were collected from the cell cultures every 3 to 4 days and tested for amp-reverse transcriptase. Procedures for PBL treatment, culturing of Canine thymocyte (Cf2th) cells and Amp reverse transcriptase activity were procedures known to those in the art. For example, see Heneine, W., et al. "Detection of reverse transcriptase by a highly sensitive assay in sera from persons infected with HIV-1." (1995). J. Infectious Diseases, 171:1201–6.

Example 2

Because of the positive Amp-reverse transcriptase activity from cells from Case 6, peripheral blood lymphocytes from Case 6 were cultured with IL-2 for 48 hours prior to addition to Canine thymocyte (Cf2th) cells. Supernatants were collected every 3 to 4 days and tested for Amp-reverse transcriptase activity. Cultures were also screened for infection of Canine thymocyte (Cf2th) by PCR amplification and probing for SFV-like DNA sequences. Each time the 1 mL sample of supernatant was taken for Amp reverse transcriptase activity, a 5 mL sample of supernatant was taken and frozen at −80° C. in order to preserve a sample of the virus producing the Amp-reverse transcriptase activity.

At day 7, Amp-reverse transcriptase testing showed a slightly positive signal in the Canine thymocyte (Cf2th) cell culture. The Canine thymocyte (Cf2th) cells were obtained from the American Type Culture Collection (Rockville, Md.). The Amp-reverse transcriptase activity increased over time. At the peak of Amp-reverse transcriptase activity cell-free supernatants were transferred to fresh Canine thymocyte (Cf2th) cells growing at $2 \times 10^5$ cells/mL. At day 4 in the new culture, cytopathic effects and syncytia was observed. Transmission electron microscopy showed vial particles in and around the cells (See FIG. 8). Viral particles were isolated from these cultures and were stored at the Centers for Disease Control and were deposited at the ATCC.

The activity in control Cf2Th cells that were treated as above, except for exposure to normal PBL instead of infected PBL, was also determined. There was no Amp-reverse transcriptase activity inherently in these Canine thymocyte (Cf2th) cells, providing evidence that there was no contamination by a retrovirus or spumavirus by the tissue culture cells.

Example 3

Case 6 has worked with non-human primates for more than 25 years. In 1977, Case 6 incurred a severe bite from a chimpanzee (B1) that required surgery and hospitalization. Retrospective analysis of twenty samples of sera archived from Case 6 between 1984 and 1988 showed the sera to have antibodies to SFVHu-6. Case 6 is in good health even after 14 years of documented SFVHu-6 infection. A serum sample recently acquired from Case 6 tested positive for SFVHu-6 antibodies by a Western blot assay. PCR analysis of PBL DNA was positive for two SFVHu-6 sequences from the gag and intergrase viral regions. Case 6's spouse tested negative for SFV-like infection by both serologic and PCR analysis despite long exposure to the SFVHu-6infected partner. The lack of sexual transmission or disease observed to date suggest a benign endpoint SFVHu-6 infection.

Having thus described the invention, numerous changes and modifications thereof will be readily apparent to those having ordinary skill in the art, without departing from the spirit or scope of the invention.

What is claimed is:

1. A spumavirus isolated from a human, comprising SEQ ID NO: 1.

2. The spumavirus of claim 1, having ATCC Deposit No. ATCC VR-2635.

3. The spumavirus of claim 1, further comprising a nucleic acid selected from the group consisting of SEQ ID NO. 3, 5, and 7.

4. The spumavirus of claim 3, wherein the spumavirus comprises SEQ ID NOs. 1 and 3.

5. The spumavirus of claim 3, wherein the spumavirus comprises SEQ ID NOs. 1 and 5.

6. The spumavirus of claim 3, wherein the spumavirus comprises SEQ ID NOs. 1 and 7.

7. The spumavirus of claim 3, wherein the spumavirus comprises SEQ ID NOs. 1, 3, and 5.

8. The spumavirus of claim 3, wherein the spumavirus comprises SEQ ID NOs. 1, 3, and 7.

* * * * *